United States Patent [19]
Zimmer

[11] Patent Number: 4,624,400
[45] Date of Patent: Nov. 25, 1986

[54] ELECTROMAGNETIC PROBE DRIVE APPARATUS

[75] Inventor: John J. Zimmer, Turtle Creek, Pa.

[73] Assignee: Westinghouse Electric Corp., Pittsburgh, Pa.

[21] Appl. No.: 544,029

[22] Filed: Oct. 21, 1983

[51] Int. Cl.⁴ .......................................... B65H 17/22
[52] U.S. Cl. .................................. 226/188; 226/154; 226/183; 242/54 A; 192/56 R
[58] Field of Search ............... 242/54 R, 54 A, 85, 242/86; 226/152, 154, 181, 183, 188; 254/134.3 R, 134.3 PA, 134.3 CL, 134.3 FT, 134.3 SC, 216, 333; 310/78; 15/315; 192/56 R, 84 E

[56] References Cited

U.S. PATENT DOCUMENTS

| 3,396,888 | 8/1968 | Rygiol | 226/152 X |
| 3,506,176 | 4/1970 | Brown | 226/183 |
| 3,585,076 | 6/1971 | Prange | 254/134.4 X |
| 3,777,964 | 12/1973 | Kruner et al. | 226/183 |
| 4,160,451 | 7/1979 | Chittenden | 242/54 A X |
| 4,293,060 | 10/1981 | Miller | 192/56 R |
| 4,449,622 | 5/1984 | Okano et al. | 310/78 X |

Primary Examiner—Harvey C. Hornsby
Attorney, Agent, or Firm—D. M. Satina

[57] ABSTRACT

An elongated flexible probe carrier is wound on a take-up reel and is fed therefrom around a feed pulley, being held in frictional engagement with the feed pulley by a plurality of idler rollers on a pivotal support arm. The feed pulley and the take-up reel are both rotatably driven from a single drive motor, respectively through two electromagnetic clutches. The take-up reel clutch is directly coupled to the motor while the feed pulley clutch is coupled to the motor either through a belt and pulley arrangement for rotation in the same direction as the motor or through a gear train for rotation in the opposite direction from the motor. A reversible motor is used with the belt and pulley type coupling. Control means are provided for selectively varying the magnetic coupling forces exerted by the two clutches for control of the feeding and take-up of the carrier without slippage. A position detecting device is coupled to the feed pulley for measuring the movement thereof.

4 Claims, 6 Drawing Figures

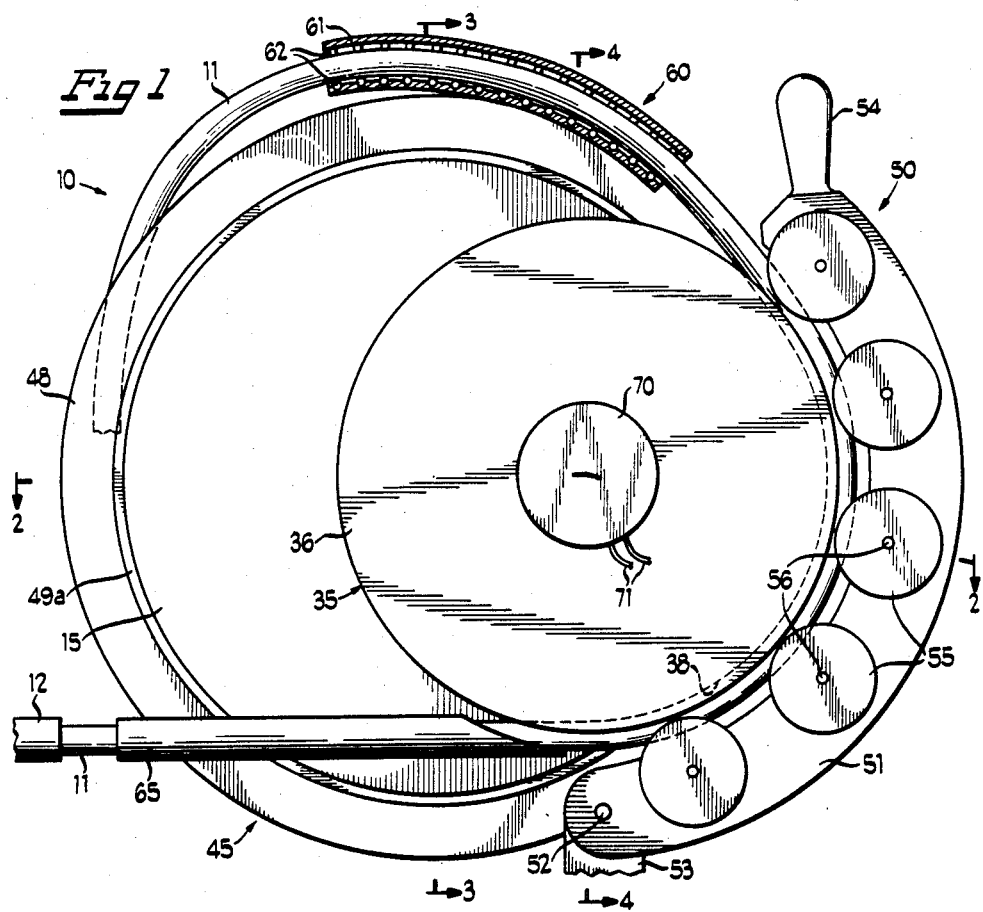

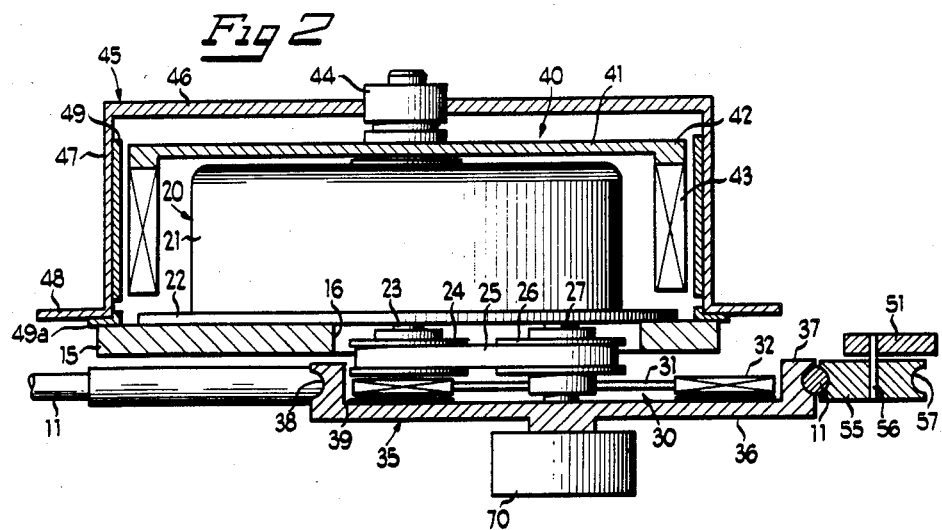
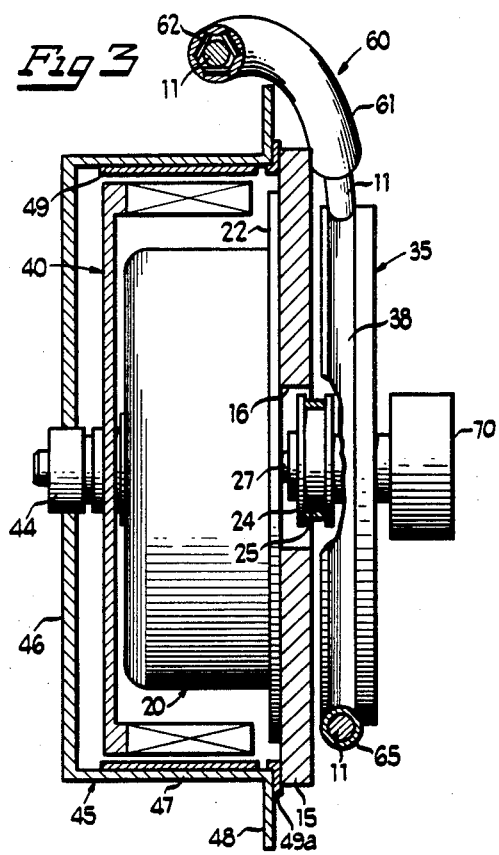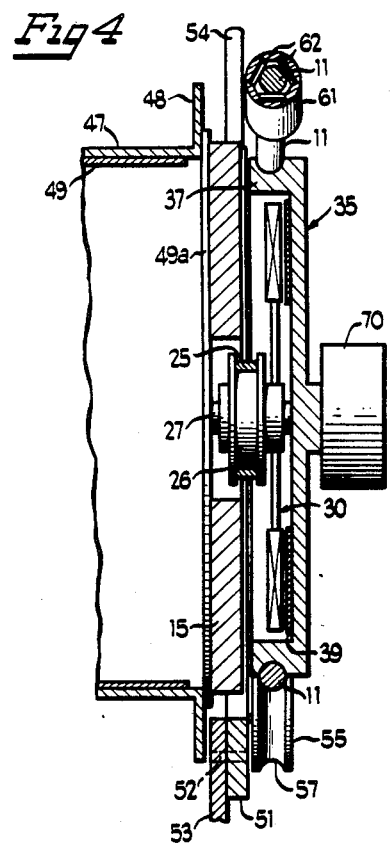

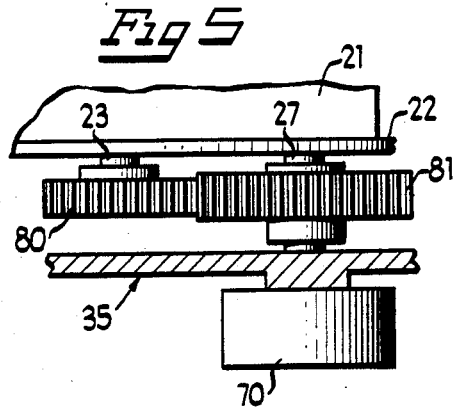
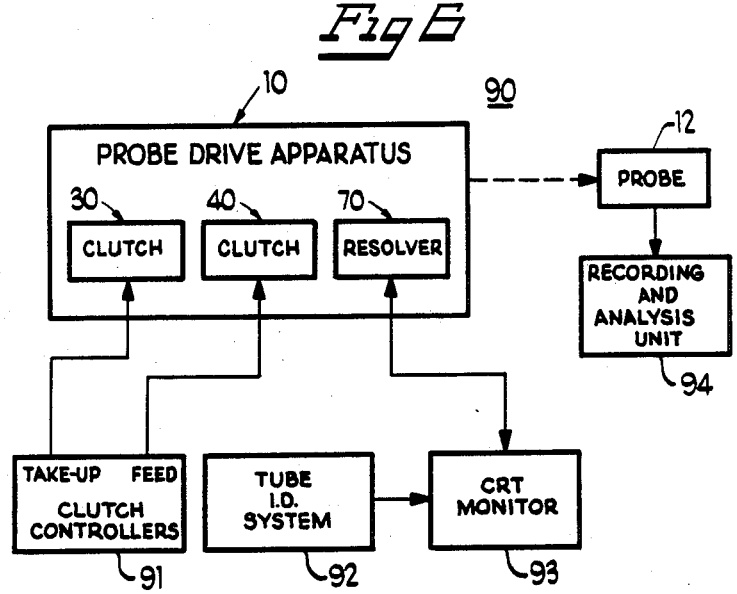

ELECTROMAGNETIC PROBE DRIVE APPARATUS

BACKGROUND OF THE INVENTION

The present invention relates generally to apparatus for delivering a measuring or detecting probe to a work position and, in particular, to apparatus for delivering a probe which is mounted on an elongated, flexible carrier.

The invention has particular application to the maintenance of a steam generator, particularly a nuclear power plant steam generator.

A typical nuclear steam generator comprises a vertically oriented vessel, a plurality of U-shaped tubes disposed in the vessel so as to form a U-shaped tube bundle, and a tube sheet for supporting the tubes at the ends opposite the U-like curvature, and a dividing plate that cooperates with the tube sheet forming a primary fluid inlet plenum at the one end of the tube bundle and a primary fluid outlet plenum at the other end of the tube bundle. The primary fluid having been heated by circulation through the nuclear reactor core enters the steam generator through the primary fluid inlet plenum. From the primary fluid inlet plenum, the primary fluid flows upwardly through first openings in the U-tubes near the tube sheet which supports the tubes, through the U-tube curvature, downwardly through second openings in the U-tubes near the tube sheet, and into the primary fluid outlet plenum. At the same time, a secondary fluid, known as feedwater, is circulated around the U-tubes in heat transfer relationship therewith, thereby transferring heat from the primary fluid in the tubes to the secondary fluid surrounding the tubes causing a portion of the secondary fluid to be converted to steam.

Isolation of the radioactive primary fluid from the secondary fluid in a nuclear steam generator is critical. Accordingly, test procedures have been developed to test the integrity of the generator tubes. One such procedure is eddy current inspection of the steam generator tubes. In this inspection process, an eddy current probe must enter and travel through a steam generator tube for approximately 60 feet and be retracted at a constant rate. The probe is mounted at the end of an elongated flexible carrier conduit through which probe conductors extend to control and recording apparatus.

The probe is fed into the tube bundle by a probe pusher which consists of a mechanical gear train driving a series of drive rollers which frictionally engage the probe carrier. These frictional rollers impart linear movement to the probe carrier and provide a slippage cluctching action in the event that the probe contacts an obstruction which impedes its passage. Thus, the frictional driving force of the drive rollers is set so that slippage will occur in the event of an obstruction so as to prevent possible damage to the probe. Retraction of the probe is accomplished by a take-up drum which is mechanically driven with a mechanical slippage clutch. Thus, in the event that the probe should become stuck upon retraction, the clutch will slip to prevent damage to the carrier and/or the probe.

A problem with this type of probe user is the frictional wear on the frictional drive rollers as a result of the slippage between the rollers and the probe carrier. This necessitates frequent replacement of the rollers. Furthermore, the probe pusher apparatus is a rather complicated mechanical device utilizing a large number of gears, bearings, ratchet drives, sprockets and the like, which results in large physical size and weight of the apparatus, complicated and expensive construction and expensive and time consuming maintenance.

Another disadvantage of that prior probe pusher apparatus is that adjustment of the tension on the roller drive must be manually effected. Thus, for example, if the probe becomes stuck so that slippage occurs in the clutch mechanism, it must be manually adjusted to apply the proper force to effect withdrawal of the probe. Also, as the clutch rollers wear, they must be periodically adjusted to maintain the proper frictional driving force. Each time such an adjustment or a parts replacement or other maintenance is performed on the apparatus, it results in exposure of maintenance personnel to radioactivity and loss of operating time. The maintenance and adjustment problem is so severe that, typically, on eddy current inspection field trips a repair person is on duty for no other reason than eddy current probe pusher maintenance.

Another drawback of the prior probe pusher apparatus is that the slippage between the drive rollers and the probe carrier prevents the measurement of probe movement by measuring the movement of the drive rollers. Thus, separate means must be provided for accurately determining the position of the probe.

SUMMARY OF THE INVENTION

It is a general object of the present invention to provide an improved apparatus for driving a probe connected to an elongated flexible probe carrier, which avoids the disadvantages of prior probe driving devices, while affording additional structural and operating advantages.

An important object of this invention is the provision of a probe driving apparatus which eliminates slippage or lost motion between the probe carrier and the driving mechanism.

Another object of this invention is the provision of an improved probe driving apparatus of the type set forth, which permits measurement of probe movement by measurement of the drive apparatus movement.

It is yet another object of this invention to provide a probe driving apparatus of the type set forth, which minimizes exposure of operating personnel to radiation.

Yet another object of this invention is the provision of a probe driving apparatus of the type set forth, which eliminates frictional wear at the interface between the driving apparatus and the probe carrier.

It is another object of this invention to provide an improved probe driving apparatus of the type set forth, which is of relatively simple and inexpensive construction and which is charcterized by low maintenance.

Still another object of the invention is the provision of a probe driving apparatus of the type set forth which is completely remotely controllable.

These and other objects of the invention are attained by providing apparatus for driving a probe connected to an elongated flexible probe carrier, the apparatus comprising a rotatable drive member having an endless drive surface, means holding the probe carrier in frictional engagement with the drive surface with a predetermined frictional force, motive means, and electromagnetic clutch means providing a magnetic coupling between the motive means and the drive member with a coupling force less than the predetermined frictional force for effecting rotation of the drive member frictionally to drive the probe carrier.

The invention consists of certain novel features and a combination of parts hereinafter fully described, illustrated in the accompanying drawings, and particularly pointed out in the appended claims, it being understood that various changes in the details may be made without departing from the spirit, or sacrificing any of the advantages of the present invention.

BRIEF DESCRIPTION OF THE DRAWINGS

For the purpose of facilitating an understanding of the invention, there are illustrated in the accompanying drawings preferred embodiments thereof, from an inspection of which, when considered in connection with the following description, the invention, its construction and operation, and many of its advantages should be readily understood and appreciated.

FIG. 1 is a side elevational view in partial section of an electromagnetic probe drive apparatus constructed in accordance with and embodying the features of the present invention;

FIG. 2 is a view in horizontal section taken along the line 2—2 in FIG. 1;

FIG. 3 is a view in vertical section taken along the line 3—3 in FIG. 1, with portions broken away to more clearly show the structure;

FIG. 4 is a fragmentary view in vertical section taken along the line 4—4 in FIG. 1, with portions of the structure removed;

FIG. 5 is a fragmentary, sectional view similar to FIG. 2, illustrating an alternative embodiment of the present invention; and FIG. 6 is a block diagrammatic view of a system incorporating the electromagnetic probe drive apparatus of the present invention.

DESCRIPTION OF THE PREFERRED EMBODIMENTS

Referring to FIGS. 1 through 4 of the drawings, there is illustrated a probe drive apparatus, generally designated by the numeral 10, constructed in accordance with and embodying the features of a first embodiment of the present invention. The probe drive apparatus 10 operates to drive a flexible probe carrier conduit 11 which has a probe 12 connected thereto at one end thereof. The probe 12 may comprise an eddy current probe, in which case electrical wires may pass through the probe carrier conduit 11. Alternatively, the probe 12 could be a fiber optic probe, in which case a fiber optic bundle would extend along the conduit 11. It will be appreciated that other types of probes could be driven with the present invention.

The probe drive apparatus 10 includes a support plate 15 which is suitably mounted on support apparatus (not shown) adjacent to the nuclear steam generator or other location where the probe is to be utilized. The support plate 15 has an opening 16 therethrough. Mounted on one side of the support plate 15 is an electric drive motor 20, which may be a reversible gear motor. The drive motor 20 has a cylindrical housing 21 and a flat circular mounting plate 22 which is fixedly secured to one side of the support plate 15 so that the output shaft 23 of the motor 20 extends through the opening 16 in the support plate 15. Fixedly secured to the end of the shaft 23 which extends through the opening 16 is a sheave or pulley 24, which is coupled by an endless drive belt 25 to another sheave or pulley 26, which is in turn fixedly secured to a shaft 27 which extends through the opening 16 and may be supported by the mounting plate 22 parallel to the motor shaft 23.

Fixedly secured to the shaft 27 is an electromagnetic clutch 30, including a circular clutch plate 31 mounted coaxially with the shaft 27 and substantially parallel to the support plate 15 and carrying at the outer periphery thereof an annular electromagnetic coil 32. Mounted coaxially with the shaft 27 for rotation with respect thereto on a suitable bearing (not shown) is a drive pulley 35. The drive pulley 35 includes a circular drive plate 36 disposed substantially parallel to the support plate 15 and provided at the peripheral edge thereof with an inwardly extending annular flange 37, which cooperates with the plate 36 to define a cup-shaped recess in which the electromagnetic clutch 30 is received. The outer surface of the flange 37 is provided with a circumferentially extending groove 38, substantially semicircular in transverse cross section, shaped and dimensioned complementary to the probe carrier conduit 11. Fixedly secured to the inner surface of the plate 36 is an annular permanent magnet 39 disposed for magnetic cooperation with the electromagnetic coil 32.

Fixedly secured to the shaft 23 at the other end thereof is an electromagnetic clutch 40, including a circular clutch plate 41 mounted coaxially with the shaft 23 and substantially parallel to the support plate 15 and provided at its peripheral edge with a forwardly extending annular flange 42 on which is mounted an annular electromagnetic coil 43. Also mounted coaxially with the shaft 23 for rotation with respect thereto by a bearing 44 is a take-up reel 45. The take-up reel 45 includes a circular plate 46 mounted coaxially with the shaft 23 and provided at its peripheral edge with a forwardly extending cylindrical wall 47 which extends substantially to the support plate 15 and cooperates therewith to enclose the drive motor 20. Integral with the cylindrical wall 47 at its forward edge is a radially outwardly extending annular flange 48. Fixedly secured to the inner surface of the cylindrical wall 47 is a cylindrical permanent magnet 49 disposed for cooperation with the electromagnetic coil 43 of the clutch 40. A frictional guide bearing 49a may be provided on the support plate 15 to guide the rotation of the take-up reel 45 with respect thereto.

Referring in particular to FIGS. 1, 2 and 4 of the drawings, the probe drive apparatus 10 also includes a retaining assembly, generally designated by the numeral 50, which include an arcuate shoe 51, part-circular in shape. One end of the shoe 51 is pivotally coupled, as at 52, to a suitable support 53, the other end of the shoe 51 being provided with a handle 54. Mounted on the shoe 51 are a plurality of rollers 55, each rotatable about an associated shaft 56 and each provided with a circumferential groove 57, shaped complementary to the probe carrier conduit 11. The shafts 56 are equidistantly spaced apart along a common circle which is coaxial with the arc of the shoe 51 and is spaced from the inner edge of the shoe 51 a distance less than the radii of the rollers 55, so that the rollers 55 extend beyond the inner edge of the shoe 51.

In operation, the shoe 51 is pivotally movable between an open or threading position (not shown), pivoted in a clockwise direction away from the drive pulley 35, as viewed in FIG. 1, and a retaining position, illustrated in FIG. 1. In this retaining position, the rollers 55 are disposed nearly tangent to the drive pulley 35 so that the grooves 57 of the rollers 55 cooperate with the groove 38 of the drive pulley 35 frictionally to grip the probe carrier conduit 11 therebetween. Thus, it will be appreciated that in this retaining position, the shoe 51, and particularly the rollers 55 thereof, operate to retain the probe carrier conduit 11 in engagement with the drive pulley 35, while the freely rotatable rollers 55 accommodate rotation of the drive pulley 35.

There is also provided a guide track assembly 60 for guiding the movement of the probe carrier conduit 11 between the drive pulley 35 and the take-up reel 45. More specifically, the guide track assembly 60 includes an elongated, relatively rigid hollow housing 61 in which is mounted plural arrays of rollers 62, the arrays being spaced apart a distance so as to define a guide path for the probe carrier conduit 11 for substantially frictionfree guiding of the movement thereof. The guide track assembly 60 may be mounted on the support plate 15 by any suitable means. There is also provided an elongated tubular guide sleeve 65 for guiding the movement of the probe carrier conduit 11 from the exit portion of the drive pulley 35 substantially tangent thereto.

The probe drive apparatus 10 is preferably also provided with a distance measuring device which may be in the form of an absolute resolver 70 mounted on the drive pulley 35 for measuring the angular rotation thereof, and thereby the linear movement of the probe carrier conduit 11, as will be explained more fully below.

Referring to FIG. 5, there is illustraterd another form of the present invention in which there is provided an alternative means for coupling the drive motor shaft 23 to the shaft 27. In this embodiment, gears 80 and 81, which are disposed in meshing engagement, are respectively fixedly secured to the shafts 23 and 27. When this drive arrangement is used, the drive motor 20 need not be reversible, for reasons which will be explained more fully below.

The operation of the probe drive apparatus 10 will now be described in detail. A supply of the probe carrier conduit 11 is wound on the cylindrical wall 47 of the take-up reel 45, the leading end of the probe carrier conduit 11 being threaded through the guide track assembly 60 to the drive pulley 35. During this initial threading operation, the retaining assembly 50 is disposed in its open position to facilitate wrapping of the probe carrier conduit 11 around the drive pulley 35 and seating in the circumferential groove 38 thereof. The probe carrier conduit 11 is then fed through the guide sleeve 65 and the retaining assembly 50 is pivoted to its closed position for securely holding the probe carrier conduit 11 in place around the drive pulley 35. Depending upon the size and nature of the probe 12, it may be coupled to the probe carrier conduit 11 either before or after this threading operation. It will be appreciated that the electrical wires or fiber optic bundle extending through the probe carrier conduit 11 are coupled at the trailing end thereof by suitable means (not shown) to associated recording equipment. The retaining assembly 50 in its closed position frictionally holds the probe carrier conduit 11 in the drive pulley groove 38.

In the embodiment of FIGS. 1-4, when it is desired to feed the probe carrier conduit 11 from the take-up reel 45, the drive motor 20 is operated in a feeding direction (clockwise, as viewed in FIG. 1), the drive belt 25 effecting a corresponding clockwise rotation of the electromagnetic clutch 30. The drive pulley 35 is not mechanically connected to the motor drive shaft 23 and, therefore, its rotation will be dependent upon the energization of the electromagnetic clutch 30. More particularly, when electrical current is applied to the electromagnetic coil 32 a magnetic field is established between the coil 32 and the permanent magnet 39 for rotating the drive pulley 35. The strength of this magnetic coupling between the clutch 30 and the drive pulley 35 is directly proportional to the current through the coil 32.

In normal operation, the clutch 30 is energized so as to produce an electromagnetic coupling force which is sufficient frictionally to drive the probe carrier conduit 11 at the desired speed, as long as the travel of the probe carrier conduit 11 is unobstructed. However, the magnetic coupling force is set so that in the event that the probe carrier conduit 11 encounters an obstruction, the electromagnetic clutch 30 will slip with respect to the drive pulley 35, stopping the rotation of the drive pulley 35 and the feeding of the probe carrier conduit 11. Sine the electromagnetic slippage is between the clutch 30 and the drive pulley 35, there is no frictional slippage between the drive pulley 35 and the probe carrier conduit 11. It will be noted that during the feeding of the probe carrier conduit 11, the take-up reel 45 rotates freely with respect to the motor shaft 23 in the same direction as the drive pulley 35, whereas the electromagnetic clutch 30 rotates with the shaft 23. While the electromagnetic clutch 40 also rotates with the motor shaft 23, it is preferably essentially deenergized.

When it is desired to retract the probe carrier conduit 11, the drive motor 20 is reversed, thereby reversing the direction of rotation of the electromagnetic clutches 30 and 40. In this case, the energization of the electromagnetic clutch 30 is minimal so that the drive pulley 35 is essentially free wheeling on the shaft 23, while the electromagnetic clutch 40 is energized to exert a magnetic coupling force on the take-up reel 45 sufficient to wind up the probe carrier conduit 11 therein. However, this coupling force is preferably not sufficient to overcome any snags or obstructions which the probe 12 or the conduit 11 might encounter during the retraction process. Should the probe carrier conduit 11 become stuck, the electromagnetic clutch 40 will thus slip with respect to the take-up reel 45, thereby stopping the retraction of the probe carrier conduit 11 and preventing any damage to the conduit 11 or the probe 12.

The embodiment of the invention illustrated in FIG. 5 operates in substantially the same manner with the exception that, in this case, the motor shaft 23 and the shaft 27 will rotate in opposite directions because of the geared coupling therebetween. Accordingly, it will be appreciated that the electromagnetic clutches 30 and 40 also rotate in opposite directions. Thus, during feeding of the probe carrier conduit 11, the drive motor 20 will rotate in a counterclockwise direction, as viewed in FIG. 1, thereby rotating the electromagnetic clutch 30 in a clockwise direction. As was the case with respect to the embodiment of FIGS. 1-4, the coupling force between the clutch 30 and the drive pulley 35 is set at a predetermined level sufficient to drive the probe 12 so as to slip in the event that the probe 12 encounters an obstruction. The electromagnetic clutch 40 may be deenergized or, if desired, may be very slightly energized to exert a slight drag on the take-up reel 45, thereby to keep the probe carrier conduit 11 taut as it is unreeled from the take-up reel 45.

When it is desired to retract the probe carrier conduit 11, reversal of the drive motor 20 is not necessary. In this case, the energization of the clutches 30 and 40 is simply changed so that a sufficient coupling force is applied to the take-up reel 35 to retract the probe carrier conduit 11, while the clutch 30 may be deenergized to allow free wheeling of the drive pulley 35.

Thus, it can be seen that the present invention provides both feeding and retraction of the probe carrier conduit 11 without any frictional slippage between the probe drive apparatus 10 and the probe carrier conduit 11. This not only eliminates wear on the probe carrier conduit 11, but also minimizes wear on the drive pulley 35. Because only a single large-diameter drive pulley is used, its speed of rotation can be substantially less than the plural small drive wheels of prior devices. It is a significant aspect of the present invention that, because there is no frictional slippage between the probe carrier conduit 11 and the probe drive apparatus 10, the linear movement of the probe carrier conduit 11 is directly proportional to the rotational movement of the drive pulley 35. Thus, the resolver 70, by measuring the angular movement of the drive pulley 35, can produce an accurate reading of the linear movement of the probe carrier conduit 11.

When the probe drive apparatus 10 is used in a system such as that illustrated in FIG. 6, the energization of the drive motor 20 and/or the electromagnetic clutches 30 and 40 is readily controllable from a remote position. Take-up and feed clutch controllers 91 are of conventional design. Thus, in the event that the probe carrier conduit 11 encounters an obstruction, the magnetic coupling forces exerted by the clutches can easily be altered remotely to exert the necessary driving forces to overcome the obstruction. No manual on-site adjustments are necessary. The output signals from the resolver 70 are fed to the tube ID system 92 which contains a programmed map of the tube bundle being investigated. Thus, when the probe motion is initiated at a predetermined reference point, the measurement of the linear probe movement by the resolver 70 results in an accurate determination of probe position at all times. This probe position may, if desired, be displayed on a CRT monitor 93. The tail end of the probe carrier conduit 11, and particularly the electrical wires or fiber scope bundles thereof, are coupled to a recording and analysis unit 94 which may permit real time data collection and analysis as the probe survey is conducted.

From the foregoing, it can be seen that there has been provided an improved probe drive apparatus which is of simple and economical construction and which effects driving of an elongated flexible probe carrier with no lost motion or slippage between the probe carrier and the driving mechanism, thereby permitting accurate direct measurement of probe movement by measuring drive apparatus motion, and substantially eliminating frictional wear of the probe carrier and the driving mechanism, while accommodating simple and accurate remote control of the apparatus.

I claim:

1. Apparatus for driving a probe through the interior of individual tubes of a nuclear reactor steam generator, said probe comprising an inspection device for said tubes and said probe connected to an elongated flexible probe carrier, said apparatus comprising:

a rotatable drive member having a cylindrical drive surface, holding means comprising an arcuate shoe member carrying a plurality of spaced idler rollers, a portion of said elongated flexible probe carrier operable to be retained between a portion of said cylindrical drive surface and said idler rollers with a predetermined frictional force in non-slipping engagement so that rotation of said cylindrical drive surface of said rotatable drive member causes said elongated flexible probe carrier to move with said cylindrical drive surface without slippage;

motive means comprising a drive motor having a motor drive shaft; and electromagnetic clutch means providing a remotely controllable and variable degree of magnetic coupling force between said motor drive shaft and said rotatable drive member for normally rotating said cylindrical drive surface of said rotatable drive member to drive said elongated flexible probe carrier and the probe connected thereto through individual ones of said tubes, and the remotely controllable coupling force exerted by said electromagnetic clutch means betweens said motor drive shaft and said rotatable drive member being maintained at less than the predetermined frictional force exerted by said holding means so that in the event motion of said probe through any of said tubes is impeded, said electromagnetic clutch means will be decoupled with respect to transmitting the motion of said motor drive shaft to said rotatable drive member thereby arresting motion of said elongated probe carrier and said probe without causing slippage between said cylindrical drive surface and the portion of said elongated probe carrier which is in contact therewith, the coupling force exerted by said electromagnetic clutch means also being remotely variable so that in the event motion of said probe through any of said tubes is impeded by an obstruction, the coupling force can be remotely increased to exert the necessary coupling force to overcome the obstruction.

2. The apparatus as specified in claim 1, wherein measurement means are coupled to said rotatable drive member for measuring the rotational movement thereof and thereby the longitudinal movement of said probe carrier.

3. The apparatus as specified in claim 1, wherein a rotatable take-up reel has wound thereon a supply portion of said probe carrier, and a second electromagnetic clutch means is magnetically coupled with a remotely variable coupling force between said motive means and said take-up reel for effecting rotation of said take-up reel to roll said probe carrier thereon when it is desired to withdraw said probe carrier and said probe from said tube being inspected.

4. The apparatus as specified in claim 3, wherein control means is coupled to both of said electromagnetic clutch means for selectively independently varying the magnetic coupling forces thereof to control the movement of said probe carrier.

* * * * *